(12) United States Patent
Lecoq

(10) Patent No.: US 7,102,135 B2
(45) Date of Patent: Sep. 5, 2006

(54) PET SCANNER

(75) Inventor: Paul Lecoq, Gex (FR)

(73) Assignee: European Organization for Nuclear Research, Geneva (CH)

( * ) Notice: Subject to any disclaimer, the term of this patent is extended or adjusted under 35 U.S.C. 154(b) by 252 days.

(21) Appl. No.: 10/696,550

(22) Filed: Oct. 29, 2003

(65) Prior Publication Data

US 2004/0129886 A1 Jul. 8, 2004

Related U.S. Application Data

(63) Continuation-in-part of application No. 09/892,201, filed on Jun. 26, 2001, now abandoned.

(51) Int. Cl.
G01T 1/20 (2006.01)
(52) U.S. Cl. .............................. 250/363.03; 250/361 R; 250/367
(58) Field of Classification Search ........... 250/363.03, 250/367, 361 R
See application file for complete search history.

(56) References Cited

U.S. PATENT DOCUMENTS

| 3,967,122 | A | * | 6/1976 | Ashe et al. .................. 250/367 |
| 4,677,299 | A | * | 6/1987 | Wong ...................... 250/363.03 |
| 4,843,245 | A | | 6/1989 | Lecomte |
| 5,213,712 | A | | 5/1993 | Dole |
| 5,319,204 | A | * | 6/1994 | Wong ...................... 250/363.03 |
| 5,399,869 | A | * | 3/1995 | Usuda ...................... 250/486.1 |
| 5,493,121 | A | * | 2/1996 | Fitzpatrick .................. 250/369 |
| 5,961,714 | A | | 10/1999 | Melcher et al. |
| 6,040,580 | A | | 3/2000 | Watson et al. |
| 6,078,052 | A | | 6/2000 | DiFilippo |
| 6,093,347 | A | | 7/2000 | Lynch et al. |
| 6,194,726 | B1 | | 2/2001 | Pi et al. |
| 6,232,605 | B1 | | 5/2001 | Soluri et al. |
| 6,288,399 | B1 | * | 9/2001 | Andreaco et al. ............ 250/368 |
| 6,303,935 | B1 | | 10/2001 | Engdahl et al. |
| 6,323,489 | B1 | * | 11/2001 | McClellan ............... 250/361 R |
| 6,362,479 | B1 | * | 3/2002 | Andreaco et al. ............ 250/366 |
| 6,437,336 | B1 | | 8/2002 | Pauwels et al. |
| 6,521,894 | B1 | | 2/2003 | Iwanczyk et al. |
| 6,528,793 | B1 | * | 3/2003 | Chen et al. ............. 250/363.03 |
| 6,534,771 | B1 | * | 3/2003 | Rozsa ......................... 250/367 |
| 6,552,348 | B1 | | 4/2003 | Cherry et al. |
| 6,921,901 | B1 | * | 7/2005 | Chai et al. ............... 250/361 R |
| 2003/0076914 | A1 | | 4/2003 | Tiller et al. |
| 2004/0200964 | A1 | * | 10/2004 | Lefaucheur et al. ..... 250/361 R |
| 2005/0269515 | A1 | * | 12/2005 | Saleh et al. ................. 250/369 |

FOREIGN PATENT DOCUMENTS

| EP | 0 219 648 B1 | 3/1990 |
| EP | 0 437 051 B1 | 5/1995 |
| WO | WO 99/24848 | 5/1999 |

OTHER PUBLICATIONS

J. Chval et al., Development of new mixed Lu x (RE3+) 1-x AP:Ce scintillators (RE3+=Y3+or Gd3+): comparison with other Ce-doped or intrinsic scintillating crystals (2000). Nuclear Instruments & Methods in Physics Research A, V. 443 pp. 331-341.*

(Continued)

Primary Examiner—Albert Gagliardi
(74) Attorney, Agent, or Firm—Dicke, Billig & Czaja, PLLC

(57) ABSTRACT

A positron emission camera comprising a plurality of scintillators, wherein the scintillators include $LuAlO_3:Ce$ ($Lu_xY_{1-x}AP$ where $0.5 \leq x \leq 0.995$) based crystals (18,20). In particular, the scintillation crystals (18,20) are $Lu_xY_{1-x}AP$ where $0.5 \leq x \leq 0.995$.

9 Claims, 3 Drawing Sheets

OTHER PUBLICATIONS

Kuntner et al., "Intrinsic Energy Resolution and Light Output of the Lu0.7Y0.3AP:Ce Scintillator", Nuclear Inst. and Methods in Phys. Res. A 493 pp. 131-136 (2002).*

M. Schmand, et al.; "Performance results of a new DOI detector block for a High Resolution PET—LSO Research Tomograph HRRT"; IEEE Conference Record; 1998; pp. 934-938.

Mares J.A., Spectroscopy and characterization of $Ce^{3+}$-doped pure or mixed $Lu_x(RE^{3+})_{1-x}AlO_3$ scintillators (Abstract), Journal of Alloys and Compounds, vol. 300-301, p. 95-100 (Apr. 2000).

* cited by examiner (a)          (b)

| Material | Density $\rho$, g/cm$^3$ | Emission maximum $\lambda$, nm | Light yield, photons/ MeV | Decay time $\tau$, ns | Photoelectric absorption coefficient @ 511 keV 1/cm |
|---|---|---|---|---|---|
| Lu$_2$SiO$_5$: Ce (LSO) | 7.4 | 420 | 27,000 | 40 | 0.30 |
| LuAlO$_3$: Ce (LuAP) | 8.34 | 380 | 9,600 | 11 (60%) | 0.31 |
| Gd$_2$SiO$_5$: Ce (GSO) | 6.7 | 440 | 8,000/1,000 | 60 for fast component 600 for slow component | 0.18 |

PET SCANNER

CROSS-REFERENCE TO RELATED APPLICATION

This application is a Continuation-In-Part of U.S. application Ser. No. 09/892,201, filed Jun. 26, 2001 now abandoned, which is incorporated herein by reference.

FIELD OF THE INVENTION

The present invention relates to a positron emission tomography (PET) camera or scanner, and to a scintillator for such a camera or scanner.

BACKGROUND OF THE INVENTION

PET scanners are well known in the field of medical physics. These scanners produce images of the body by detecting radiation emitted from radioactive substances injected into the body. Each scanner is made up of radiation detectors, typically called scintillators, which are arranged in a ring configuration around a movable patient table. A typical arrangement with a detector ring 10 and a patient table 12 is shown in FIG. 1. Each scintillator comprises a crystal and has an associated partner located opposite it on the ring. Many known cameras use $Bi_4Ge_3O_{12}$ (BGO) as a scintillation detector, as taught in U.S. Pat. No. 4,843,245 and EP 0,437,051 B. Each scintillator is connected to a photomultiplier tube, which is in turn connected to read-out electronics.

During a scan the patient is positioned on the movable table in the centre of the ring of detectors. The patient is injected with a radioactive substance, which is tagged with a $\beta^+$ radioactive atom that has a short decay time, for example carbon-11, fluorine-18, oxygen-15 or nitrogen-13. During decay of the nuclei of the radioisotopes, positrons are given off. When a positron is emitted and meets an electron, the collision produces two gamma rays that have the same energy, 511 keV, but travel in opposite directions. By detecting coincidentally the gamma rays generated using scintillators that are diametrically opposed on the ring, the trajectory on which the disintegration occurred can be detected. The scintillator crystals convert the gamma rays to photons of light that are transmitted to the photomultiplier tubes, which convert and amplify the photons to electrical signals. These electrical signals are then processed by a computer to generate three dimensional images of the body over the region of interest (e.g. brain, breast, liver).

An advantage of PET scanning is the ability to determine accurately radionuclide localization and to quantify physiological processes in the body. This can be done because of the emission from the patient's body of two gamma photons that travel in opposite directions. Another advantage is that PET scanners use biological compounds similar or identical to those found in the human body, such as carbon, nitrogen, and oxygen. This means that the PET radionuclides can be substituted directly into biological substances used by the body. In addition, it means that PET tracers do not merely mimic biological pathways as do agents for some other scanners, instead PET tracers actually follow true physiological and metabolic processes. This is advantageous. In contrast, other nuclear medicine imaging techniques require compounds labelled with radioactive nuclides not commonly found in the body. These modified compounds only approximate the true distribution in the human body.

Because of the many advantages inherent in PET scanners, there is a drive to improve their performance, thereby to increase the accuracy of the scanned images and so assist clinicians. To this end, work is presently being done by many groups to improve the characteristics of such scanners.

The most important characteristics of a PET camera are its spatial resolution and sensitivity. Conventional PET cameras can provide spatial resolutions in the range of 4–6 mm at full width half maximum (FWHM) of the emission spectrum. Better spatial resolution requires a large number of scintillation detectors with reduced size, and as a consequence, a large number of photodetectors and associated read-out electronics. This, however, increases the cost. At the same time, new demands on human PET instrumentation, for example on precise brain imaging, require spatial resolution to be better than 2 mm.

The combined formula for a reconstructed image resolution for a PET scanner can be expressed as follows:

$$\Gamma = 1.254\sqrt{(d/2)^2 + (0.0022D)^2 + r^2 + b^2}$$

Here $\Gamma$ is the reconstructed image resolution in mm FWHM, d is detector size, D is the detector array diameter, which is typically 600–800 mm for a whole body PET scanner and 250–300 mm for a brain PET (NB including D takes into account photon non-collinearity from positron decay), r is the effective positron range (from 0.5 mm for $^{18}F$ to 4.5 mm for $^{82}Rb$), and b is an additional factor, which is derived from a hit point identification scheme (Anger Logic or "true" position sensitive photo detector, i.e: analog ratios among many photomultiplier signals). Assuming that b is zero for a position sensitive photodetector, it is possible to achieve (with $^{18}F$) $\Gamma=1$ mm resolution for brain a PET at d=1 mm.

In addition to limitations on the spatial resolution of known PET scanners, there is also a geometrical limitation on the spatial resolution at the end of a PET scanner field of view. This is the so-called radial elongation distortion, which occurs when gamma trajectories cross several scintillation detectors.

Assuming that the above equation is accurate, in order to satisfy the growing demand on the spatial resolution and sensitivity of PET cameras, it will be appreciated that the camera has to be made of thin detectors with high stopping power. In practice, however, the stopping power being limited by the density of the material the detector needs to have a certain length, typically one to three centimetres which reduces the spatial resolution at the edge of the field of view. This is a disadvantage. To overcome this problem and avoid degradation of the spatial resolution, it is necessary to use a detector with depth of interaction (DOI) determination capability, i.e. the ability to determine the interaction coordinate along the detector cell. The most convenient way to do this is to use a multi-layer detector, in which the layers are made of material with different scintillation properties. Because the layers have different characteristics, when a gamma ray is detected it is possible to identify the layer that was hit and so determine more accurately the interaction point.

Many multi-layer detectors are known. For example, U.S. Pat. No. 4,843,245 describes a multi-layer scintillator that uses adjacent BGO and GSO ($Gd_2SiO_5$) crystals. EP 0,219, 648 teaches the use of a three layer scintillator that has an inner layer of $BaF_2$, a middle layer of GSO and an outer layer of BGO. WO 99/24848 also teaches the use of a multi-layer detector and in particular a "phoswich" detector, in which different detector layers are made of different scintillators with different decay times. The phoswich described in WO 99/24848 has two layers, one each of BGO and $Lu_2SiO_5$:Ce (LSO).

Another known multi-layer detector uses a combination of LSO and GSO. In this case, hit layer determination is carried out using pulse shape discrimination. This can be done because of the large difference in decay time constants of the LSO and GSO layers. Unfortunately, the photoelectric absorption coefficient of GSO is much less than that of LSO. This means that the stopping power of the GSO is limited, which introduces a degree of uncertainty into the determination of the hit layer.

In yet another known PET, the scintillation detectors are made of layers of "fast" and "slow" LSO scintillators, grown with different cerium concentrations.

As with the LSO and GSO detectors, pulse shape discrimination is used to determine the hit layer. A disadvantage of this particular device is, however, that the difference in decay time constants of "fast" and "slow" LSO is only about 10% (4–5 nanoseconds at mean value of 40 ns). Hence, there can be difficulty in determining the hit layer with any certainty.

SUMMARY OF THE INVENTION

According to one aspect of the present invention, there is provided a positron emission tomography camera or scanner comprising: a patient area, a detector ring for detecting radiation from opposite sides of the patient area, the ring including a plurality of scintillation detectors directed towards the patient area, the scintillation detectors being such as to emit light when radiation is incident thereon, and converting means optically coupled to the scintillation detectors for converting light emitted by the scintillation detectors to electrical pulses, wherein each of the plurality of scintillation detectors comprises lutetium-yttrium-aluminate-perovskite, $Lu_xY_{1-x}AP$ (where $0.5 \leq x \leq 0.995$).

In an embodiment each of the scintillation detectors comprises at least one further scintillating layer.

In an embodiment each of the scintillation detectors comprises at least one further layer of material disposed adjacent the lutetium-yttrium-aluminate-perovskite, the said material comprising one of the group comprising LSO, BGO, GSO, LGSO, YAP, YSO and LYSO.

In an embodiment each of the scintillation detectors comprise said $Lu_xY_{1-x}AP$ as a first layer and at least one further layer disposed adjacent the first layer, the further layer comprising $Lu_xY_{1-x}AP$ wherein for said at least one further layer the value of x is selected to provide appropriate differences in the time constant to the time constant of the $Lu_xY_{1-x}AP$ of the first layer.

In an embodiment, determining means are provided for determining whether detected radiation was incident on the lutetium-yttrium-aluminate-perovskite or the at least one further layer.

In an embodiment, the determining means are operable to analyse the electrical signal to determine a pulse shape, the pulse shape being indicative of whether detected radiation was incident on the lutetium-yttrium-alurinate-perovskite or the at least one further layer.

In an embodiment, a respective optical element is disposed between each scintillation detector and its associated converting means, the optical element being such that light from the lutetium-yttrium-aluminate-perovskite is affected in one way and light from the at least one further layer is affected in another way.

In an embodiment, the camera or scanner further comprises at least one optical element, the optical element being disposed to receive light from at least two scintillation detectors and being constructed and arranged so that light from the lutetium-yttrium-aluminate-perovskite is affected in one way and light from the at least one further layer is affected in another way.

In an embodiment, the optical element is a wavelength divider.

In an embodiment, the wavelength divider comprises at least one of the group comprising a glass filter, an interference filter, a diffraction grating, a prism, a diffractive micro-optic array and a refractive micro-optic array.

In an embodiment, the converting means comprise at least one photomultiplier tube.

In an embodiment, the or each photomultiplier tube is position sensitive.

In an embodiment, the converting means comprise one of photodiodes and avalanche photodiodes.

In an embodiment, the converting means comprise one of silicon photodiodes and avalanche silicon photodiodes.

According to a second aspect of the invention there is provided a positron emission tomography camera or scanner comprising a plurality of scintillators, wherein the scintillators comprise lutetium-yttrium-aluminate-perovskite, $Lu_xY_{1-x}AP$ (where $0.5 \leq x \leq 0.995$).

In an embodiment, the scintillators additionally comprise a layer of material positioned adjacent the lutetium-yttrium-aluminate-perovskite, wherein said material comprises one of the group comprising LSO, GSO, BGO, LGSO, YAP, YSO and LYSO.

According to a further aspect of the invention there is provided a scintillator for use in the camera or scanner of the first or second aspects, wherein the scintillator comprises lutetium-yttrium-aluminate-perovskite, $Lu_xY_{1-x}AP$ (where $0.5 \leq x \leq 0.995$).

BRIEF DESCRIPTION OF THE DRAWINGS

Various cameras and scintillators in which the invention is embodied will now be described by way of example only and with reference to the accompanying drawings, of which.

DESCRIPTION OF PREFERRED EMBODIMENTS

The PET in which the invention is embodied uses scintillators that comprise lutetium based crystals. In particular, the scintillator in which the invention is embodied uses lutetium-yttrium-aluminate-perovskite, with the proportions of Lu and Y defined by $Lu_xY_{1-x}AP$ (where $0.5 \leq x \leq 0.995$). This material has many properties that make it useful as a scintillator; hereinafter it is referred to as Lu YAP.

Figure 1:
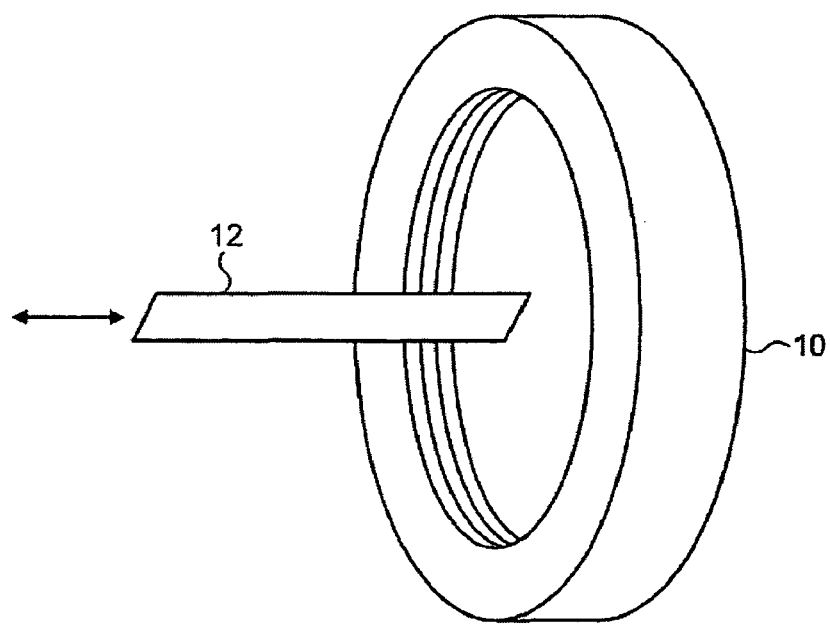
FIG. 1 is a perspective view of a ring and table.
Figure 2:
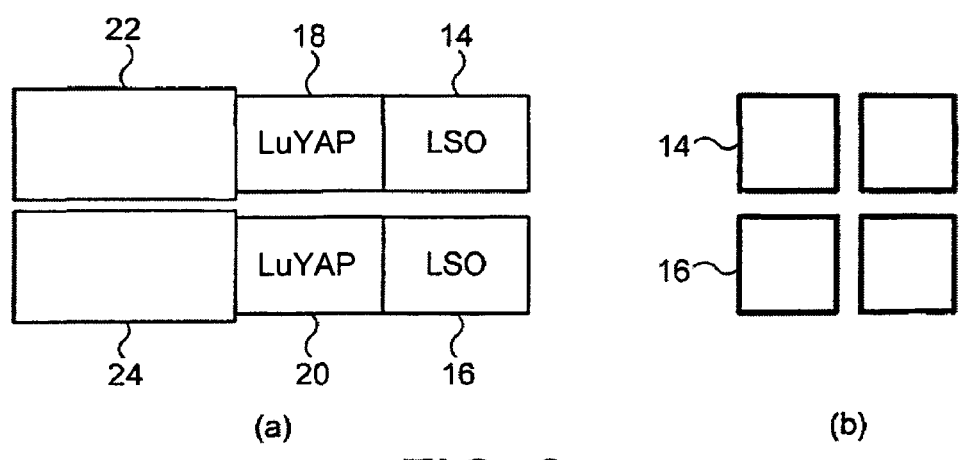
FIG. 2(a) is a side view of a first detector for use in a PET.
FIG. 2(b) is a front view on arrow A of FIG. 2(a)

FIGS. 2(a) and (b) show two scintillators for a PET scanner, each of which comprises an inner layer of LSO 14,16 and a layer of LuYAP 18,20. Each layer of LSO and LuAP is preferably less than 20 mm thick. Adjacent each LuYAP layer 18, 20 and optically coupled thereto is a photodetector 22,24 for detecting light emitted either from the LSO 14,16 or the LuAP 18,20. The photodetectors 22,24 can be of any suitable type, but typically include photomultipliers or avalanche photodiodes. Signals from the photodetectors 22,24 are processed using read-out electronics (not shown). In practice, a plurality of the scintillators and photodetectors shown in FIG. 2 are provided in a ring configuration around a patient table, in accordance with conventional layout for PET scanners. Using signals from the photodetectors, an image of the tissue being scanned can be constructed.

The use of LuYAP in the scanner of FIGS. 2(*a*) and (*b*) provides various benefits. This is because of the advantageous crystal characteristics of LuYAP.

Figures 3, 4:
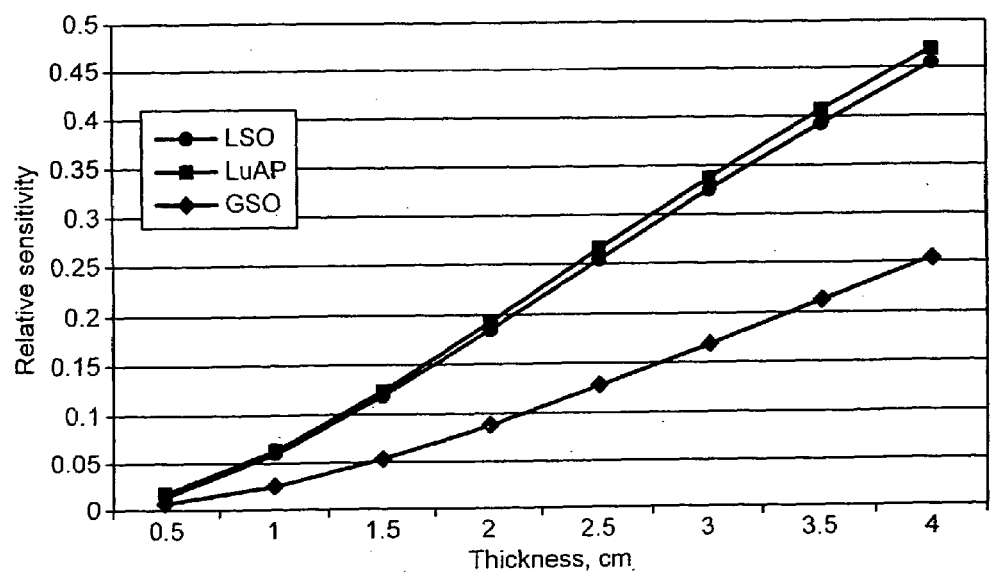
FIG. 3 shows a table that includes various scintillation characteristics of LSO, LuYAP and GSO scintillators.
FIG. 4 is a plot of calculated relative sensitivities of PET scanners based on LSO, LuYAP and GSO scintillators, at $E_\gamma$=511 keV, vs crystal thickness.

Relative properties of LuYAP, LSO and GSO are shown in the table of FIG. 3, from which it can be seen that the photoelectric absorption coefficient of LuYAP at 511 keV is 0.31, which is comparable to LSO which has a photoelectric absorption coefficient of 0.30. In contrast, the photoelectric absorption coefficient for GSO is 0.18. This means that the effective stopping power of GSO is significantly less than that of either of LSO or LuYAP. In addition, the decay constant for LuYAP is 11 ns for 60 percent of the emitted light, whereas for LSO it is 40 ns. This is a relatively large difference. This is advantageous for the LSO/LuYAP scintillator of FIG. 2, because it means that pulse width discrimination can be used to accurately determine the hit layer. A further advantage of the LSO/LuYAP device of FIG. 2 is that LuYAP is transparent to LSO scintillation light. This means that light emitted from the inner LSO layer can pass substantially unimpeded through the LuYAP to the photodetector. This improves the sensitivity of the detection process.

Relative sensitivities of PET scanners that use rings of LuYAP, LSO and GSO scintillators respectively are shown as a function of crystal thickness in FIG. 4. It should be noted that the relative probability of detecting double coincidence of photo absorption events is taken as a measure of the PET ring sensitivity.

From FIG. 4, it can be seen that the sensitivity of a PET scanner that uses GSO scintillators is much less than that for a scanner using LuYAP scintillators (comparing scanners of the same size). Hence, the dual layer LSO/LuYAP scintillator of FIG. 2 can be made more sensitive than a conventional LSO/GSO scintillator of the same size. Alternatively, the same sensitivity can be obtained using a significantly thinner LSO/LuYAP scintillator. This is advantageous, because it means that the overall size of the PET scanner can be reduced, as can the associated cost. In particular, for a dual layer detector made of LSO/LuYAP and a dual layer detector made of LSO/GSO, the same level of sensitivity can be obtained when the LuYAP layer is about 1.7 times thinner than a layer of GSO. This means that the PET scanner made of LSO/LuYAP has better spatial resolution at the end of the field of view than a scanner made from LSO/GSO and the cost is likely to be lower, because the volume of crystal needed is reduced.

Figure 5:
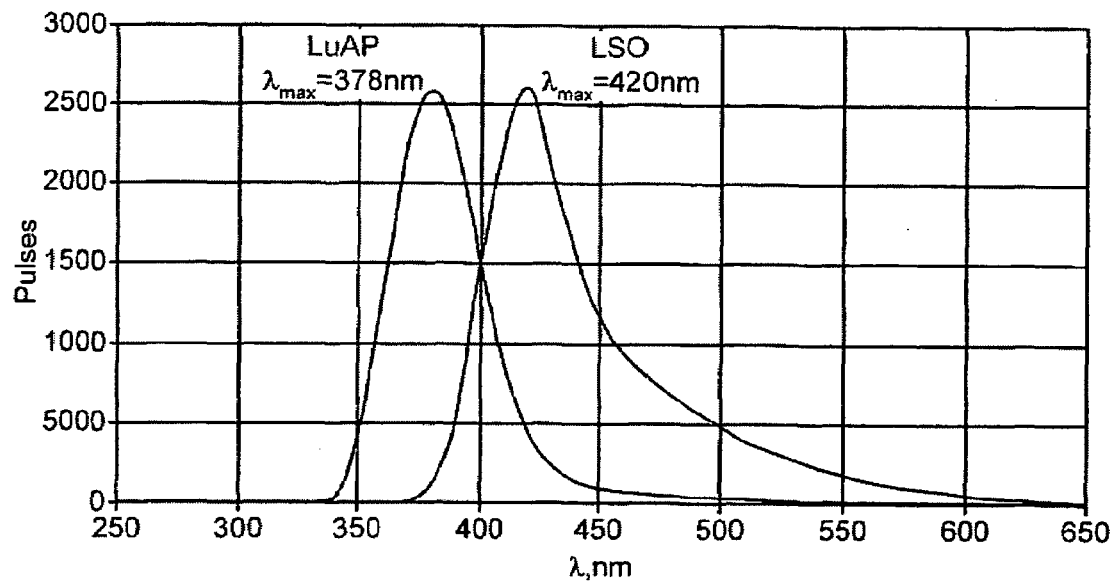
FIG. 5 shows emission spectra for LSO and LuYAP.
Figure 6:
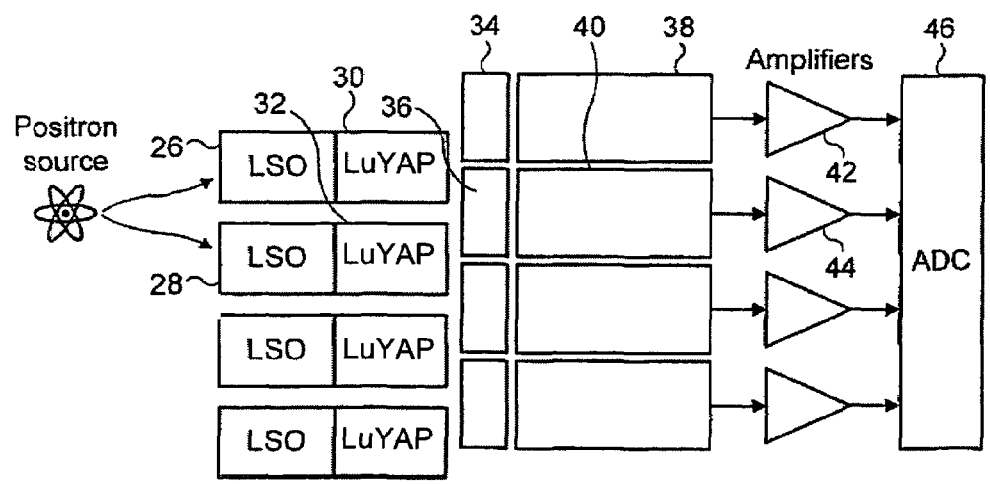
FIG. 6 is a block diagram of a second detector for use in a PET.

FIG. 5 shows emission spectra for each of LSO and LuYAP. From this is can be seen that the LSO spectra has a maximum of 420 nm and the LuYAP spectra has a maximum of 378 nm. Hence, if the light detected by the photodetectors of FIG. 2 is at 378 nm, this indicates that the LuYAP was hit, whereas if the light detected is at 420 nm, this indicates that the LSO was hit. This means that in addition to using pulse width discrimination, the spectral selection of the emission for the scintillator of FIG. 2 can be used to identify the hit layer. This can be done by detecting the "colour" of the light that reaches the photodetector. FIG. 6 shows a detector that is adapted to detect the colour of the light.

FIG. 6 shows plurality of like scintillators for a PET camera, each of which has a LSO layer 26,28 and a LuYAP layer 30,32. As before, each layer of LSO 26,28 and LuAP 30,32 is preferably less than 20 mm thick. Adjacent the scintillators are a plurality of wavelength division elements 34,36. Each of these is physically offset relative to the scintillators, so that it spans, by equal amounts, two adjacent scintillation detectors. Adjacent wavelength dividers 34 and 36 have different transmission coefficients. This means that the end of each scintillator is adjacent two different wavelength dividers 34 and 36. The wavelength division elements 34 and 36 can be made of coloured glass filters. In the example of FIG. 6, filter 34 is transparent for light emissions from both of the LSO and the LuYAP layers 26 and 30 respectively, whereas filter 36 is transparent for emissions from the LuYAP layer 26 and semi-transparent for emissions from the LSO layer 26. Hence, whilst the filter 34 affects light from the different scintillation layers to the same extent, the filter 36 affects light from the LuYAP layer in one way and light from the LSO layer in another way.

To detect scintillation light from the scintillators of FIG. 6, photodetectors 38 and 40 are optically coupled to the wavelength dividers 34,36. Each photodetector 38,40 is physically offset relative to the scintillation detectors, but substantially in line with its associated wavelength divider 34,36, so that it spans two adjacent scintillation detectors. Coupled to each photodetector 38,40 is an amplifier 42,44 for amplifying its output. Signals from the amplifiers 42,44 are output to an analogue to digital converter 46 for processing. The processed signals are used to construct an image of the material being scanned.

To provide a PET scanner, a plurality of the scintillators and photodetectors shown in FIG. 6 are provided in a ring configuration around a patient table, in accordance with the conventional practice.

When the LuYAP detector 30 of FIG. 6 is hit, the amplitudes of the electrical pulses from photodetectors 38 and 40 are equal. This is because the wavelength dividers 34 and 36 are each transparent to LuYAP scintillation light. In contrast, when the LSO detector 26 is hit, the amplitude of the electrical pulse from the photodetector 38 is higher than that of photodetector 40. This is because the wavelength divider 34 is transparent to LSO scintillation light, whereas the wavelength divider 36 is only semi-transparent to such light. Hence, by comparing the amplitudes of the pulses detected by the photodetectors, the hit layer can be identified.

Whilst the wavelength dividers 34 and 36 of FIG. 6 comprise a glass filter, they could equally be any one or more of an interference filter and/or a diffraction grating and/or a prism and/or a diffractive micro-optic array and/or a refractive micro-optic array.

In summary, the present invention is directed to the use of a new high-sensitivity crystal, LuYAP, which when applied to a PET camera provide greater image sharpness, due to the decreased size of the scintillation detector. The PET is less expensive, more sensitive and has relatively low angulation degradation of the spatial resolution, thereby allowing the diameter of the detector ring to be decreased, which in turn reduces the overall cost of the camera. Furthermore, in a dual layer configuration the large difference in decay time constants of LSO and LuYAP (40 ns and 11 ns for 60 percent of the emitted light respectively) makes pulse shape discrimination a useful option and allows effective hit layer determination.

Other embodiments of the present invention relate to scintillators for PET cameras or scanners, and to PET cameras or scanners having scintillators in which a layer of LuYAP (as defined above) is adjacent another material adapted to scintillate, wherein the another material may be one of the group comprising LSO, BGO, LGSO, YAP, YSO and LYSO. In other embodiments, there are two or more layers of LuYAP, with the proportions of Lu to Y in each layer being selected to give different time constants ($Lu_xY_{1-x}AP$ with x selected to be different in adjacent layers to afford the requisite time constant performance)

A skilled person will appreciate that variations of the disclosed arrangements are possible without departing from the invention. Accordingly, the description of the specific embodiments is made by way of example and not for the purposes of limitation. It will be clear to the skilled person that minor modifications can be made without significant changes to the operation described above.

The invention claimed is:

1. A positron emission tomography camera or scanner comprising:
   a patient area,
   a detector ring for detecting radiation from opposite sides of the patient area, the ring including a plurality of scintillation detectors directed towards the patient area, the scintillation detectors being such as to emit light when radiation is incident thereon, and
   converting means optically coupled to the scintillation detectors for converting light emitted by the scintillation detectors to electrical pulses,
   wherein each of the plurality of scintillation detectors comprises lutetium-yttrium-aluminate-perovskite, $Lu_xY_{1-x}AP$ (where $0.5 \leq x \leq 0.995$).

2. The positron emission tomography camera or scanner of claim 1, wherein each of the scintillation detectors comprise at least one further layer of material disposed adjacent the lutetium-yttrium-aluminate-perovskite, the said material comprising one of the group comprising LSO, GSO, BGO, LGSO, YAP, YSO and LYSO.

3. The camera or scanner of claim 2, wherein determining means are provided for determining whether detected radiation was incident on the lutetium-yttrium-aluminate-perovskite or the at least one further layer.

4. The camera or scanner of claim 2, wherein determining means are provided for analyzing the electrical signal to determine a pulse shape, the pulse shape being indicative of whether detected radiation was incident on the lutetium-yttrium-aluminate-perovskite or the at least one further layer.

5. The camera or scanner of claim 1, wherein the converting means comprise at least one photomultiplier tube.

6. The camera or scanner of claim 5, wherein the or each photomultiplier tube is position sensitive.

7. The camera or scanner of claim 1, wherein the converting means comprise one of photodiodes and avalanche photodiodes.

8. A positron emission tomography camera or scanner comprising:
   a patient area,
   a detector ring for detecting radiation from opposite sides of the patient area, the ring including a plurality of scintillation detectors directed towards the patient area, the scintillation detectors being such as to emit light when radiation is incident thereon, and
   converting means optically coupled to the scintillation detectors for converting light emitted by the scintillation detectors to electrical pulses,
   wherein each of the plurality of scintillation detectors comprises lutetium-yttrium-aluminate-perovskite, $Lu_xY_{1-x}AP$ (where $0.5 \leq x \leq 0.995$), and
   wherein each of the scintillation detectors comprise said $Lu_xY_{1-x}AP$ as a first layer and at least one further layer disposed adjacent the first layer, the further layer comprising $Lu_xY_{1-x}AP$ wherein for said at least one further layer the value of x is selected to provide appropriate differences in the time constant of the $Lu_xY_{1-x}AP$ of the first layer and the electrical pulse shape of the $Lu_xY_{1-x}AP$ of the first layer.

9. The camera or scanner of claim 8, wherein determining means are provided for analyzing the electrical signal to determine a pulse shape, the pulse shape being indicative of whether detected radiation was incident on the lutetium-yttrium-aluminate-perovskite or the at least one further layer.

* * * * *